US012672982B2

(12) United States Patent
Spottheim

(10) Patent No.: US 12,672,982 B2
(45) Date of Patent: Jul. 7, 2026

(54) MEDICAL DRESSING

(71) Applicant: Ofer Spottheim, Raanana (IL)

(72) Inventor: Ofer Spottheim, Raanana (IL)

( * ) Notice: Subject to any disclaimer, the term of this patent is extended or adjusted under 35 U.S.C. 154(b) by 243 days.

(21) Appl. No.: 18/021,597

(22) PCT Filed: Aug. 16, 2021

(86) PCT No.: PCT/IL2021/050995
§ 371 (c)(1),
(2) Date: Feb. 16, 2023

(87) PCT Pub. No.: WO2022/038599
PCT Pub. Date: Feb. 24, 2022

(65) Prior Publication Data
US 2023/0293352 A1     Sep. 21, 2023

Related U.S. Application Data

(60) Provisional application No. 63/066,251, filed on Aug. 16, 2020.

(51) Int. Cl.
*A61F 13/02* (2024.01)
*A61F 13/00* (2024.01)
(Continued)

(52) U.S. Cl.
CPC .... *A61F 13/0233* (2013.01); *A61F 13/00063* (2013.01); *A61F 13/0246* (2013.01);
(Continued)

(58) Field of Classification Search
CPC ................ A61F 13/00; A61F 13/00021; A61F 13/00063; A61F 13/0233; A61F 13/0246; A61F 13/0243; A61F 13/0253; A61F 13/0266; A61F 2013/00391; A61F 2013/00604; A61F 2013/00089; A61F 2013/00744; A61F 2013/53062;
(Continued)

(56) References Cited

U.S. PATENT DOCUMENTS 3,313,473 A * 4/1967 Witters .................. B65D 33/20
                                                      229/80
4,399,816 A     8/1983 Spangler
(Continued)

FOREIGN PATENT DOCUMENTS

AU        2014101354 A4    12/2014
CA           2401590 A1 *  8/2001   .............. A61P 31/02
(Continued)

OTHER PUBLICATIONS

Cn 110381930A machine translation (Year: 2019).*

*Primary Examiner* — Caitlin A Carreiro
(74) *Attorney, Agent, or Firm* — The Roy Gross Law Firm, LLC; Roy D. Gross

(57)                    ABSTRACT

A medical dressing composed of a continuous frame enclosing a first surface area and having a bottom surface coated with an adhesive material and an upper surface, a polyurethane layer having a second surface area which covers the first surface area and is larger than the first surface area, and a layer opaque to UV rays having a third surface area, which covers the second surface area and is equal or larger than the second surface area.

17 Claims, 2 Drawing Sheets

(51) Int. Cl.

| | |
|---|---|
| *A61F 13/0246* | (2024.01) |
| *A61L 15/26* | (2006.01) |
| *A61L 15/42* | (2006.01) |

(52) U.S. Cl.
CPC ............. *A61L 15/26* (2013.01); *A61L 15/425* (2013.01); *A61F 2013/00391* (2013.01); *A61F 2013/00604* (2013.01)

(58) Field of Classification Search
CPC ........... A61F 2013/00582; A61L 15/26; A61L 15/425; A61L 2300/00
USPC .............. 602/41–43, 45, 48, 52, 54, 58, 900
See application file for complete search history.

(56) References Cited

U.S. PATENT DOCUMENTS

| | | | |
|---|---|---|---|
| 5,000,741 A | | 3/1991 | Kalt |
| 5,562,107 A | * | 10/1996 | Lavender .............. A61F 15/008 |
| | | | 602/41 |
| 7,265,256 B2 | | 9/2007 | Artenstein |
| 7,988,673 B2 | | 8/2011 | Wright et al. |
| 9,387,127 B2 | | 7/2016 | Apolet et al. |
| 10,369,058 B2 | * | 8/2019 | Ha ......................... A61F 13/025 |
| 2005/0107732 A1 | | 5/2005 | Boyde |
| 2009/0177135 A1 | | 7/2009 | Rogers et al. |
| 2010/0256545 A1 | | 10/2010 | Aali et al. |
| 2011/0015557 A1 | | 1/2011 | Aali et al. |
| 2013/0102945 A1 | | 4/2013 | Long |
| 2023/0293352 A1 | | 9/2023 | Spottheim |

FOREIGN PATENT DOCUMENTS

| | | | | |
|---|---|---|---|---|
| CN | 110381930 A | * | 10/2019 | .............. A61P 43/00 |
| EP | 2995324 A1 | | 3/2016 | |
| JP | 2005246046 A | | 9/2005 | |
| JP | 2007275185 A | | 10/2007 | |
| WO | 2005104661 A2 | | 11/2005 | |
| WO | 2019168844 A1 | | 9/2019 | |
| WO | 2020051548 A1 | | 3/2020 | |

* cited by examiner

MEDICAL DRESSING

CROSS-REFERENCE TO RELATED APPLICATIONS

This application is a National Phase of PCT Patent Application No. PCT/IL2021/050995 having International filing date of Aug. 16, 2021, which claims the benefit of priority of U.S. Patent Application No. 63/066,251, filed on Aug. 16, 2020, both entitled "MEDICAL DRESSING", the contents of which are all incorporated herein by reference in their entirety.

FIELD OF THE INVENTION

The present invention, in some embodiments thereof, relates to medical dressings and medical dressing kits.

BACKGROUND OF THE INVENTION

A wound is a disruption in the continuity of the epithelial lining of the skin or mucosa resulting from physical or thermal damage and/or other pathological reasons. The wound can be categorized as acute or chronic. An acute wound is an injury to the skin that occurs suddenly due to accident or surgical injury. It normally heals at a predictable and expected time frame usually within 4-15 weeks depending on the size, depth and the extent of damage to the epidermis and dermis layer of the skin. Chronic wounds on the other hand fail to progress through the normal stages of healing and cannot be repaired in an orderly and timely manner. Chronic wounds generally result from decubitus ulcers, leg ulcers and burns.

Wound healing is a dynamic and complex process of tissue regeneration and growth progress through four different phases (i) the coagulation and homeostasis phase (immediately after injury); (ii) the inflammatory phase, (shortly after injury to tissue) during which swelling takes place; (iii) the proliferation period, where new tissues and blood vessels are formed and (iv) the maturation phase, in which remodeling of new tissues takes place. These phases occur in an ordered manner overlapping with each other in a well-connected cascade. Promotion of these phases are largely depending on the wound type, and its associated pathological conditions and the type of dressing material.

With the advancement in technology, currently, different types of wound dressing materials are available for all types of wounds. But the selection of a material for a particular wound is important to achieve faster healing. In this review, an attempt has been made to consolidate the different types of wound dressing materials and their function on healing process. Optimal wound dressings assure a moist wound bed, help drainage, remove debris from the wound surface, provide optimal thermal stability, might be removed without trauma of the wound bed and wound edge, and be antial-lergenic and without immunogenicity. Furthermore, materials included in the wound dressing adhesive should also be hypoallergenic.

Wound dressings have gone through continuous developments over the years which emanate from a more detailed understanding of wound healing and improved technological, clinical, and scientific research in the field of wound healing. Wound dressings today are functionalized to a targeted therapy by including different active compounds. Those active compounds optimize the wound-healing process.

Medicated dressings incorporate drugs and are important in the healing process directly or indirectly by removal of necrotic tissues. Antimicrobials prevent infection and promotes tissue regeneration. Some commonly incorporated compounds include antimicrobial agents, growth factors and enzymes.

Silver impregnated dressings available are Fibrous hydro-colloid, Polyurethane foam film and silicone gels. Antiseptic Iodine dressing acts on bacterial cells via oxidative degradation of cell components by interrupting the function of protein, which is widely effective against pathogen. Prolong usage of iodine leads to skin irritation and staining. The purpose of antimicrobials is mainly to prevent or combat infections especially for diabetic foot ulcers.

Normal tissue repair process in the body is controlled by cellular activities caused by growth factors that are naturally present in our body. In case of chronic wounds, growth factors and cells are arrested in the wound bed within the clots that affects the healing process.

Among the different growth factors, platelet derived growth factor (PDGF) is the most commonly used growth factor which promotes chemotactic recruitment and proliferation of cells and increasing angiogenesis. Besides, PDGF, fibroblast growth factor (FGF), epidermal growth factor (EGF), and autologous platelet thrombin are also studied extensively for their application in the healing process. Among which, PDGF and EGF are approved by FDA for human application.

Composite dressings are versatile and convenient for both partial and full thickness wounds. A composite or combination dressings has multiple layers and each layer is physiologically distinct. Most of the composite dressings possess three layers.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in accordance with some embodiments, a medical dressing comprising: (a) a continuous frame enclosing a first surface area and having a bottom surface comprising an adhesive material and an upper surface, the frame is 0.1 to 2 cm thick; (b) a layer comprising polyurethane having a second surface area, the second surface area covers said first surface area and is equal or larger than the first surface area, the layer comprising polyurethane is at least partially non-reversibly connected to the continuous frame; and (c) a layer opaque to UV rays having a third surface area, the third surface area covers the second surface area and is larger than the second surface area, the layer opaque to UV rays is at least partially reversibly connected to the continuous frame, a top surface of the layer comprising polyurethane, or both, wherein the layer opaque to UV rays, said layer comprising polyurethane, or both comprises a pull-tab.

In some embodiments, the layer opaque to UV rays, the layer comprising polyurethane, or both has a thickness of between 50 and 1000 $\mu$m.

In some embodiments, the continuous frame is impermeable to the passage of liquid, bacterium a virus, or any combination thereof.

In some embodiments, the layer comprising polyurethane is porous.

In some embodiments, porous is characterized by pore size of 0.1 to 1 μm.

In some embodiments, the continuous frame, the layer opaque to UV rays, the layer comprising polyurethane or any combination thereof comprises an antimicrobial substance, an anti-infective agent, polyhexamethylene biguanide, chlorhexidine, silver, iodine, iodophor, benzalkonium chloride, hydrogen peroxide, an antibiotic, a debridement agent, an analgesic, a wound healing factor, a nitric oxide releasing material, a matrix metalloproteinase inhibitor, a vitamin, a growth factor, a cannabinoid, a terpene, or any combination thereof.

In some embodiments, the layer opaque to UV rays comprises a metallized surface.

In some embodiments, the bottom surface of: the layer opaque to UV rays, the layer comprising polyurethane or any combination thereof, contacts a non-woven-fabric surface.

In some embodiments, the non-woven-fabric comprises natural fibers, semi-natural fibers, fibers synthetic fibers, or any combination thereof.

In some embodiments, the continuous frame comprises non-woven fabric felts, synthetic material felts, fiber flocks, or any combination thereof.

In some embodiments, the at least partially reversibly connected comprises: a first surface comprising reversibly connecting adhesive and a second surface comprising non-reversibly connecting adhesive.

In some embodiments, the ratio of surface area comprising reversibly connecting adhesive and surface area comprising non-reversibly connecting adhesive is 2:1 to 10:1.

In some embodiments, the surface comprising non-reversibly connecting adhesive of, the layer opaque to UV rays, the layer comprising polyurethane or any combination thereof is located in a perimetrical area of the continuous frame.

In some embodiments, the layer opaque to UV rays, the layer comprising polyurethane or both is flexible.

There is also provided, in accordance with some embodiments, a method for protecting a topical lesion, comprising applying the medical dressing on the topical lesion, wherein the continuous frame surrounds at least a portion of the topical lesion, thereby protecting a topical lesion.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF THE INVENTION

According to an aspect of some embodiments of the present invention there is provided a medical dressing comprising: (a) a continuous frame enclosing a first surface area and having a bottom surface comprising an adhesive material and an upper surface; (b) a layer comprising polyurethane having a second surface area; and (c) a layer opaque to UV rays having a third surface area. In one embodiment, the medical dressing comprising: (a) a continuous frame enclosing a third surface area and having a bottom surface comprising an adhesive material and an upper surface; (b) an upper layer; and (c) a bottom layer having a third surface area.

Figure 1:
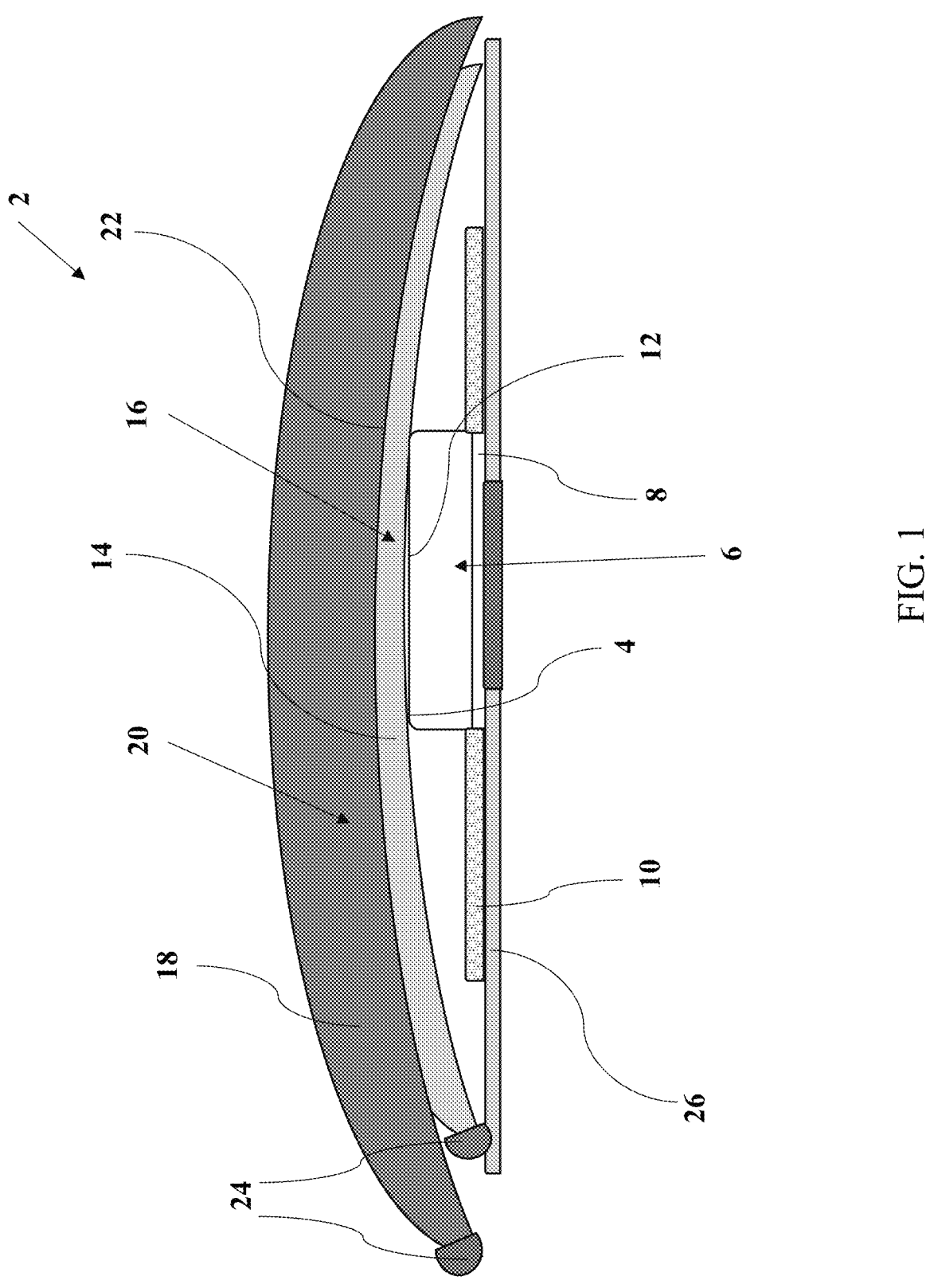
FIG. 1 is a plan view simplified illustration of the medical dressing, in accordance with some embodiments of the invention.

In one embodiment, there is provided a medical dressing such as medical dressing 2 of FIG. 1. In one embodiment, medical dressing 2 comprises: (a) a continuous frame enclosing a first surface area and having a bottom surface comprising an adhesive material and an upper surface; (b) a layer comprising polyurethane having a second surface area, said second surface area covers the first surface area and is equal or larger than the first surface area, the layer comprising polyurethane is at least partially non-reversibly connected to said continuous frame; and (c) a layer opaque to UV rays having a third surface area, said third surface area covers said second surface area and is larger than the second surface area, the layer opaque to UV rays is at least partially reversibly connected to said continuous frame, a top surface of the layer comprising polyurethane, or both, wherein the layer opaque to UV rays, the layer comprising polyurethane, or both comprises a pull-tab. In one embodiment, the frame is 0.1 to 2 cm thick. In one embodiment, a first surface area is first surface area 6. In one embodiment, a second surface area is second surface area 16. In one embodiment, a third surface area is third surface area 20. In one embodiment, a pull-tab is pull-tab 24. In one embodiment, an adhesive material is adhesive material 10. In one embodiment, a top surface of the layer comprising polyurethane is top surface of the layer comprising polyurethane 22. In one embodiment, a continuous frame is continuous frame 4.

In some embodiments, adhesive material 10 is applied to one side of medical dressing 2.

Figure 2:
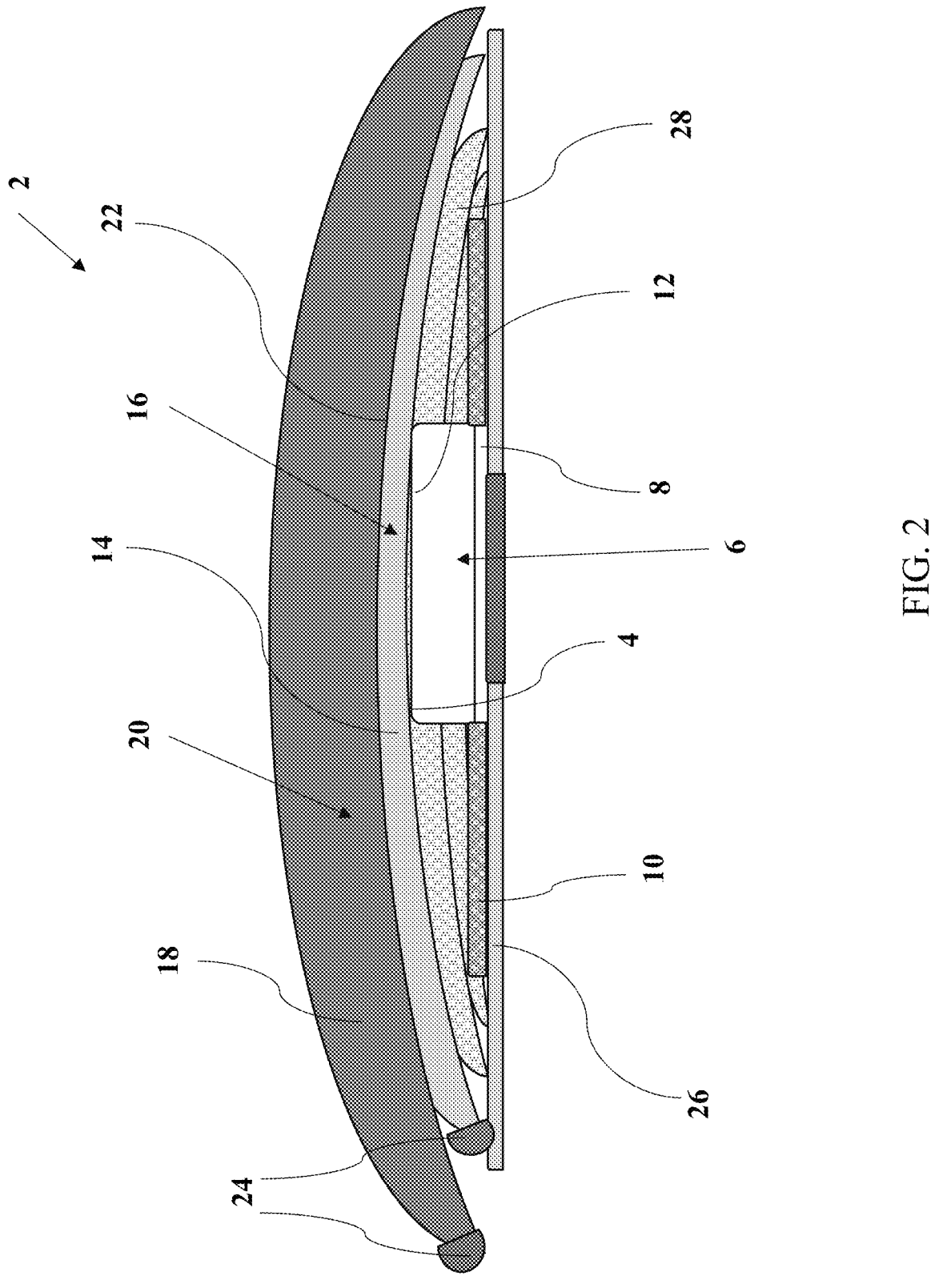
FIG. 2 is a plan view simplified illustration of the medical dressing comprises a non-woven-fabric, in accordance with some embodiments of the invention.

In one embodiment, a non-woven-fabric is non-woven-fabric 28. In one embodiment, non-woven-fabric 28 comprises a felts. In one embodiment, non-woven-fabric 28 comprises a surface. As can be seen in FIG. 2, in one embodiment, medical dressing 2 comprises non-woven-fabric 28. In one embodiment, layer opaque to UV 18 contacts a non-woven-fabric 28. In one embodiment, layer comprising polyurethane 14 contacts a non-woven-fabric 28. In one embodiment, medical dressing 2 comprises a non-woven-fabric felts. In one embodiment, medical dressing 2 comprises a non-woven-fabric surface.

In one embodiment, any one of first surface area 6 and one or more non-woven-fabrics 28 include material configured to absorb unwanted wound secretion, for example, by capillary forces. In such case, the wound area in body tissue 26 may be drained and evacuated from unwanted excess wound secretion.

In one embodiment, provided herein is a medical dressing comprising: (a) a continuous frame enclosing a first surface area and having a bottom surface comprising an adhesive material and an upper surface (b) a layer opaque to UV rays having a second surface area, the second surface area covers the first surface area and is equal or larger than the first surface area, the layer opaque to UV rays is at least partially reversibly connected to the continuous frame, and (c) a layer comprising polyurethane having a third surface area, the third surface area covers said second surface area and is larger than the second surface area said layer comprising polyurethane is at least partially reversibly connected to: an upper portion of the layer opaque to UV rays, the continuous frame or both, wherein each of the layer opaque to UV rays and the layer comprising polyurethane comprises a pull-tab.

In one embodiment, continuous frame 4 comprises a synthetic polymer. In one embodiment, continuous frame 4 comprises at least 80% w/w a synthetic polymer. In one embodiment, continuous frame 4 comprises at least 85% w/w a synthetic polymer. In one embodiment, continuous frame 4 comprises at least 90% w/w a synthetic polymer. In one embodiment, continuous frame 4 comprises at least 95% w/w a synthetic polymer.

In one embodiment, a synthetic polymer comprises: gauze, tulle. In one embodiment, a synthetic polymer comprises occlusive or semi-occlusive polymer. In one embodiment, a synthetic polymer is in the form of a film, foams, hydrogel, hydrocolloid, or any combination thereof.

In one embodiment, a synthetic polymer traps exudate, hence providing a moist environment for wounds. In one embodiment, a synthetic polymer comprises Polyurethane (PU). In one embodiment, a synthetic polymer is impermeable to bacteria and liquid. In one embodiment, a synthetic polymer is permeable to moisture vapor and air.

In one embodiment, continuous frame 4 comprises a foam. In one embodiment, continuous frame 4 comprises a Polyurethane foam. In one embodiment, continuous frame 4 comprises a hydrophilic polymeric foam. In one embodiment, continuous frame 4 comprises non-woven fabric felts. In one embodiment, the continuous frame 4 comprises synthetic material felts. In one embodiment, continuous frame 4 comprises fiber flocks.

In one embodiment, a bottom surface is bottom surface 8. In one embodiment, bottom surface 8 is adapted to adhere or to connect to a skin tissue such as skin tissue 26. In one embodiment, bottom surface 8 is adapted to adhere or to connect to a mucosa. In one embodiment, an upper surface is upper surface 12. In one embodiment, upper surface 12 is adapted to be covered by a layer such as described herein. In one embodiment, upper surface 12 is connected and/or adhered to a layer such as described herein. In one embodiment, a layer comprising polyurethane is layer comprising polyurethane 14. In one embodiment, a layer opaque to UV is layer opaque to UV 18. In one embodiment, a layer comprises layer comprising polyurethane 14, layer opaque to UV 18, or both.

In some embodiments, the medical dressing 2 includes a self-sealing film (not illustrated) located from example between bottom surface 8 and surface 6. In some embodiments, the self-sealing film may be located between continuous frame 4 and second surface area 16. In one embodiment, the self-sealing film may include any medical grade polymer configured to be penetrated by a needle attached to a syringe that upon extraction of the needle is self sealed. In one embodiment, a needle of a syringe may penetrate the medical dressing 2 through the self-sealing film for aspiration of an exudate (e.g., unwanted wound secretion). Once the exudate is aspirated the needle is withdrawn and the self-sealing film would seal the puncture in the film due to its inherent properties 26.

In some embodiments, the medical dressing 2 includes one or more channels for collecting exudate, for example, in low to medium exuding wounds. In one embodiment, the one or more channels (not illustrated) include a tube laminated to the bottom surface 8 facing skin tissue 26. In one embodiment, the one or more channels (e.g., one or more gauge tubes) may be located between surface 8 and surface 6. In such cases, at least first opening of the one or more channels may be located substantially in the middle of surface 8 and at least one second opening may be outside medical dressing 2, for example, in proximity to pull-tab 24. In one embodiment, the second opening may include a connector and/or a cap for connecting the channel to a syringe or a suction device. In such case, the syringe may be used for aspirating the exudate collected under the dressing.

In one embodiment, the one or more channels are laminated to the surface using any suitable adhesive (e.g., a hypoallergenic adhesive). In one embodiment, the one or more channels are threaded to the surface. In one embodiment, the one or more channels are laminated/adhered/threaded between surface 8 and surface 6.

In one embodiment, one, two, three or more channels may be laminated to the medical dressing. In one embodiment, the channels may be made from any suitable polymer, for example, medical grade polyethylene, medical grade polycarbonate and the like. In one embodiment, the internal diameter of each channel may be between 0.5 mm to 5 mm. In one embodiment, the diameter may be 1 mm. In one embodiment, the diameter may be 1.5 mm.

In one embodiment, the diameter may be 2 mm. In one embodiment, the diameter may be 2.5 mm. In one embodiment, the diameter may be 3 mm. In one embodiment, the diameter may be 4 mm.

In one embodiment, a layer comprises a bottom layer and an upper layer. In one embodiment, a bottom layer comprises a layer opaque to UV. In one embodiment, an upper layer comprises a layer opaque to UV a layer opaque to UV. In one embodiment, a bottom layer comprises a layer comprising polyurethane. In one embodiment, an upper layer comprises a layer opaque to UV a layer comprising polyurethane. In one embodiment, an upper layer is adhered or connected to the bottom layer and/or to the continuous frame. In one embodiment, a bottom layer is adhered or connected to the upper layer and/or to the continuous frame.

In one embodiment, a layer is irreversibly or partially reversibly adhered or connected to: an upper surface, the continuous frame or both. In one embodiment, a layer is reversibly adhered to: an upper surface, the continuous frame or both. In one embodiment, a layer comprises a surface irreversibly adhered to: an upper surface, the continuous frame or both. In one embodiment, a layer comprises a surface reversibly adhered to: an upper surface, the continuous frame or both. In one embodiment, a layer comprises a surface irreversibly adhered to: an upper surface, the continuous frame or both and a surface reversibly adhered to: an upper surface, the continuous frame or both. In one embodiment, partially reversibly connected includes a layer comprising a surface irreversibly adhered to: an upper surface, the continuous frame or both and a surface reversibly adhered to: an upper surface, the continuous frame or both. In one embodiment, connected comprises adhered.

In one embodiment, irreversibly adhered or connected results in irreversible connection. In one embodiment, reversibly adhered or connected results in reversible connection.

In one embodiment, partially reversibly connected comprises at least partially reversibly. In one embodiment, partially reversibly connected comprises: reversibly connecting two surfaces in one region and non-reversibly connecting the same two surfaces in a second region. In one embodiment, partially reversibly connected comprises: a first surface comprising a reversibly connecting adhesive and a second surface comprising non-reversibly connecting adhesive.

In one embodiment, the ratio of a first surface area or one region comprising reversibly connecting adhesive and a second surface area or second region comprising non-reversibly connecting adhesive is 1:1 to 20:1. In one embodiment, the ratio of a first surface area or one region comprising reversibly connecting adhesive and a second surface area or second region comprising non-reversibly connecting adhesive is 2:1 to 10:1. In one embodiment, the ratio of a first surface area or one region comprising reversibly connecting adhesive and a second surface area or second region comprising non-reversibly connecting adhesive is 1:1 to 5:1. In one embodiment, the ratio of a first surface area or one region comprising reversibly connecting adhesive and a second surface area or second region comprising non-reversibly connecting adhesive is 2:1 to 6:1. In one embodiment, the ratio of a first surface area or one region comprising reversibly connecting adhesive and a second surface area or second region comprising non-reversibly connecting adhesive is 2:1 to 4:1. In one embodiment, first surface and second surface are two separate surface areas. In one embodiment, one region and second region are distinct regions.

In one embodiment, the second surface comprising non-reversibly connecting adhesive of the bottom layer, the upper layer opaque to UV rays, the layer comprising polyurethane, or any combination thereof is located in a perimetrical area of the continuous frame. In one embodiment, the second surface comprising non-reversibly connecting adhesive of the bottom layer, the upper layer opaque to UV rays, the layer comprising polyurethane, or any combination thereof is located in a distinct face or side within the perimetrical area of the continuous frame.

In one embodiment, an adhesive or adhesive comprises a pressure sensitive adhesive, a structural adhesive, or a combination thereof. In one embodiment, an adhesive or adhesive comprises a removable adhesive. In one embodiment, an adhesive is adapted to adhere by mechanical means. In one embodiment, an adhesive or adhesive is adapted to adhere by electrostatic forces. In one embodiment, an adhesive or adhesive is adapted to adhere by van der Waals' force. In one embodiment, an adhesive or adhesive is adapted to adhere by moisture-aided diffusion of the glue into the substrate (such as skin). In one embodiment, an adhesive or adhesive comprises an acrylic adhesive. In one embodiment, an adhesive comprises a hydrocolloid. In one embodiment, an adhesive or adhesive comprises a hydrogel. In one embodiment, an adhesive or adhesive comprises silicone. In one embodiment, an adhesive or adhesive comprises rubber. In one embodiment, an adhesive or adhesive comprises latex. In one embodiment, an adhesive or adhesive comprises a synthetic rubber. In one embodiment, an adhesive or adhesive comprises Polyurethane. In one embodiment, an adhesive or adhesive comprises a soft silicone. In one embodiment, an adhesive or adhesive comprises a Cyanoacrylate.

In one embodiment, an adhesive or the adhesive seals anchors the frame or the dressing to a patient's skin. In one embodiment, the adhesive material is a hypoallergenic material.

In one embodiment, a bottom layer comprises a second surface area, wherein the second surface area covers the third surface area and is equal or larger than the third surface area. In one embodiment, an upper layer comprises a third surface area, wherein the third surface area covers the second surface area and is equal or larger than the third surface area, second are, or both.

In one embodiment, a bottom layer, an upper layer, a layer opaque to UV rays, a layer comprising polyurethane, or any combination thereof has a thickness of between 50 and 1000 µm. In one embodiment, a bottom layer, an upper layer, a layer opaque to UV rays, a layer comprising polyurethane, or any combination thereof has a thickness of between 100 and 500 µm. In one embodiment, a bottom layer, an upper layer, a layer opaque to UV rays, a layer comprising polyurethane, or any combination thereof has a thickness of between 100 and 250 µm. In one embodiment, a bottom layer, an upper layer, a layer opaque to UV rays, a layer comprising polyurethane, or any combination thereof has a thickness of between 100 and 800 µm. a bottom layer, an upper layer, a layer opaque to UV rays, a layer comprising polyurethane, or any combination thereof has a thickness of between 150 and 350 µm. In one embodiment, a bottom layer, an upper layer, a layer opaque to UV rays, a layer comprising polyurethane, or any combination thereof has a thickness of between 250 and 750 µm.

In one embodiment, the medical dressing, continuous frame, upper layer, bottom layer or any combination thereof is impermeable to a passage of a liquid, a bacterium a virus, or any combination thereof. In one embodiment, the medical dressing, continuous frame, upper layer, bottom layer or any combination thereof is permeable to a passage of gasses.

In one embodiment, the continuous frame, the bottom layer, the upper layer, or any combination thereof is porous. In one embodiment, porous is characterized by pore size of 0.1 to 1 µm. In one embodiment, porous is characterized by pore size of 0.1 to 0.5 µm. In one embodiment, porous is characterized by pore size of 0.2 to 0.8 µm. In one embodiment, porous is characterized by pore size of 0.3 to 0.6 µm.

In one embodiment, the continuous frame, the bottom layer, the upper layer, the layer opaque to UV rays, said layer comprising polyurethane or any combination thereof comprises an antimicrobial substance, an anti-infective agent, polyhexamethylene biguanide, chlorhexidine, silver, iodine, iodophor, benzalkonium chloride, hydrogen peroxide, an antibiotic, a debridement agent, an analgesic, a healing factor, a nitric oxide releasing material, a matrix metalloproteinase inhibitor, a vitamin, a growth factor, a cannabinoid, a terpene, or any combination thereof.

In one embodiment, the layer opaque to UV rays comprises a metallized surface. In one embodiment, the layer opaque to UV rays comprises a densely woven dark cloth. In one embodiment, the layer opaque to UV rays comprises a polyester. In one embodiment, the layer opaque to UV rays comprises a lightweight satiny silk. In one embodiment, the layer opaque to UV rays is a cloth, a film or a layer coated with an organic or an inorganic ultraviolet (UV) filter.

In one embodiment, a bottom surface of the bottom layer, a bottom surface of the layer comprising polyurethane, or any combination thereof contacts or is adhered to a non-woven-fabric surface. In one embodiment, a non-woven-fabric comprises natural fibers, semi-natural fibers, fibers synthetic fibers, or any combination thereof.

In one embodiment, the layer opaque to UV rays, the layer comprising polyurethane, the bottom layer, the upper layer, or any combination thereof is flexible. In one embodiment, the layer opaque to UV rays, the layer comprising polyurethane, the bottom layer, the upper layer, or any combination thereof is solid. In one embodiment, the layer opaque to UV rays, the layer comprising polyurethane, the bottom layer, the upper layer, or any combination thereof is semi-rigid. In one embodiment, the frame is rigid.

In one embodiment, the layer opaque to UV rays, the layer comprising polyurethane, the bottom layer, the upper layer, or any combination thereof comprises a pull-tab. In one embodiment, the pull-tab in the bottom layer is on one side of the bottom layer and the pull-tab in the upper layer is on the opposite side.

In one embodiment, the layer opaque to UV rays, the layer comprising polyurethane, the bottom layer, the upper layer, or any combination thereof comprises a pull-tab. In one embodiment, the pull-tab is adjacent to a reversible connection. In one embodiment, the pull-tab is adjacent to both a reversible connection and an irreversible connection. In one embodiment, the pull-tab is adjacent or bordered by a reversible connection.

In one embodiment, the frame is 0.05 to 2 cm thick. In one embodiment, the frame is 0.1 to 0.5 cm thick. In one embodiment, the frame is 0.1 to 2 cm thick. In one embodiment, the frame is 0.1 to 0.8 cm thick. In one embodiment, the frame is 0.3 to 0.8 cm thick. In one embodiment, the frame has a width of 0.01 to 0.5 cm. In one embodiment, the frame has a width of 0.02 to 0.4 cm. In one embodiment, the frame has a width of 0.05 to 0.1 cm. In one embodiment, the frame has a width of 0.01 to 0.1 cm.

In one embodiment, the frame may have a variety of shapes, including: spherical, cuboidal, triangular, pyramidal, cylindrical and conical shapes.

In one embodiment, provided herein is a method for protecting a topical lesion, comprising applying the medical dressing as described herein the topical lesion, wherein the continuous frame surrounds at least a portion of the topical lesion, thereby protecting a topical lesion.

In one embodiment, the adhesive is located on a bottom surface of the frame (facing the wound). In one embodiment, the adhesive forms a perimeter around the lesion and hold the frame in place on a lesion. In one embodiment, the adhesive is on the outer perimeter of frame and is adapted to adhere the medical dressing to a topical surface.

In one embodiment, there is no need to remove and dispose of the frame after the dressing is applied to the lesion. In one embodiment, the medical dressing provides a sealed environment over a lesion or other body site. In one embodiment, sealed environment includes a hermetic seal between the skin (lesion), frame and the bottom layer. In one embodiment, the medical dressing as described herein is capable of maintaining a vacuum of 80 mmHg or 100 mmHg and perhaps a vacuum as much as 200 mmHg.

In one embodiment, the present invention provides a medical dressing kit, the kit comprising, separately a frame, a bottom layer and an upper layer. In one embodiment, the present invention provides a medical dressing kit, the kit comprising, separately a frame, a bottom layer, an upper layer and a medicament. In one embodiment, the present invention provides a medical dressing kit, the kit comprising, separately: (a) a frame; and (b) a bottom layer connected to an upper layer. In one embodiment, the frame comprises means to connecting the frame to the bottom layer the upper layer, or both.

In some embodiments, the frame may comprise absorbent material to absorb fluids (e.g., liquids) entering the sealed environment. In one embodiment, an absorbent material comprise, but not limited to, hydrophilic foams, woven materials, nonwoven materials, etc. and combinations thereof.

In one embodiment, an adhesive or the adhesive applied to the frame and is adapted to connect or adhere the frame to a topical surface such as skin, comprises an adhesive polymeric film including polyurethanes, polyether polyesters, polyether amides, polyolefins, or any combination thereof. In one embodiment, the medical dressing, includes a film adhering or connecting the frame to a topical surface such as skin, comprising an adhesive polymeric film including but not limited to polyurethanes, polyether polyesters, polyether amides, polyolefins, or any combination thereof.

In one embodiment, the frame comprises a thermoplastic polymer. In one embodiment, the frame comprises polyethylene. In one embodiment, the frame comprises polyolefins, natural or synthetic rubbers, styrene butadiene rubber, butyl rubber, polyisoprene, polyisobutylene, polybutadiene, polychloroprene, acrylonitrile/butadiene, carboxyl or hydroxyl modified rubbers, silicones, polydimethylsiloxanes, styrenic block copolymers, styrene-isoprene-styrene, styrene-ethylene/butylene-styrene block copolymer, polyurethanes, or any combination thereof.

In one embodiment, the frame and/or the bottom layer comprises a surface comprising an absorbent material—absorbent surface. In one embodiment, absorbent surface comprises woven or nonwoven cotton or rayon. In one embodiment, absorbent surface comprises an antimicrobial agent, a drug for transdermal drug delivery, a chemical indicator or any combination thereof. In one embodiment, absorbent surface comprises: an antimicrobial substance, an anti-infective agent, polyhexamethylene biguanide, chlorhexidine, silver, iodine, iodophor, benzalkonium chloride, hydrogen peroxide, an antibiotic, a debridement agent, an analgesic, a healing factor, a nitric oxide releasing material, a matrix metalloproteinase inhibitor, a vitamin, a growth factor, a cannabinoid, a terpene, or any combination thereof.

In one embodiment, any adhesive or connection described herein is at least partially covered or covered with a release liner. In one embodiment, a release liner is made of kraft paper, glassine paper, polyethylene, polypropylene, polyester or composites of any of these materials.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A medical dressing comprising:
(a) a continuous frame enclosing a first surface area, said continuous frame comprises a bottom surface comprising an adhesive material, and an upper surface, wherein said continuous frame is 0.1 to 2 cm thick;

(b) a layer comprising polyurethane having a second surface area, said second surface area covers said first surface area and is equal or larger than said first surface area, said layer comprising polyurethane is partially non-reversibly connected to said continuous frame, wherein said partially non-reversibly connected comprises: a reversibly connecting adhesive and a non-reversibly connecting adhesive, and wherein said non-reversibly connecting adhesive is located in a distinct face or side within a perimetrical area of the continuous frame, and wherein the ratio between areas of said reversibly connecting adhesive and said non-reversibly connecting adhesive is 2:1 to 10:1; and (c) a layer opaque to UV rays having a third surface area, said third surface area covers said second surface area and is larger than said second surface area, said layer opaque to UV rays is at least partially reversibly connected to: said continuous frame, a top surface of said layer comprising polyurethane, or both, wherein said layer opaque to UV rays, said layer comprising polyurethane, or both comprises a pull-tab.

2. The medical dressing of claim 1, wherein said layer comprising polyurethane is porous.

3. The medical dressing according to claim 2, wherein said porous layer comprising polyurethane is characterized by a pore size of 0.1 to 1 μm.

4. The medical dressing of claim 1, wherein a bottom surface of said layer comprising polyurethane contacts a non-woven-fabric surface.

5. The medical dressing according to claim 4, wherein said non-woven-fabric surface comprises natural fibers, semi-natural fibers, fibers synthetic fibers, or any combination thereof.

6. The medical dressing of claim 1, further comprising one or more channels laminated to the bottom surface of said continuous frame.

7. The medical dressing of claim 6, wherein the one or more channels include at least one first opening located at a middle of the bottom surface and at least one second opening located outside the medical dressing.

8. The medical dressing according to claim 1, wherein said layer opaque to UV rays, said layer comprising polyurethane or both has a thickness of between 50 and 1000 μm.

9. The medical dressing of claim 1, wherein said continuous frame is impermeable to a passage of a liquid, a bacterium, a virus, or any combination thereof.

10. The medical dressing of claim 1, wherein said continuous frame has an aqueous solution absorbance capacity.

11. The medical dressing of claim 1, wherein said continuous frame, said layer opaque to UV rays, said layer comprising polyurethane or any combination thereof comprises an antimicrobial substance, an anti-infective agent, polyhexamethylene biguanide, chlorhexidine, silver, iodine, iodophor, benzalkonium chloride, hydrogen peroxide, an antibiotic, a debridement agent, an analgesic, a healing factor, a nitric oxide releasing material, a matrix metalloproteinase inhibitor, a vitamin, a growth factor, a cannabinoid, a terpene, or any combination thereof.

12. The medical dressing of claim 1, wherein said layer opaque to UV rays comprises a metallized surface.

13. The medical dressing of claim 1, wherein said continuous frame comprises non-woven fabric felts, synthetic material felts, fiber flocks, or any combination thereof.

14. The medical dressing of claim 1, wherein said second surface area comprising non-reversibly connecting adhesive of said layer opaque to UV rays, said layer comprising polyurethane or both is located in a perimetrical area of said continuous frame.

15. The medical dressing of claim 1, wherein said layer opaque to UV rays, said layer comprising polyurethane or both is solid and flexible.

16. The medical dressing of claim 1, further comprising a self-sealing film.

17. A method for protecting a topical lesion, comprising applying a medical dressing on the topical lesion, wherein a continuous frame surrounds at least a portion of said topical lesion, thereby protecting said topical lesion, wherein the medical dressing comprises:

(a) a continuous frame enclosing a first surface area, said continuous frame comprises a bottom surface comprising an adhesive material, and an upper surface, wherein said continuous frame is 0.1 to 2 cm thick;

(b) a layer comprising polyurethane having a second surface area, said second surface area covers said first surface area and is equal or larger than said first surface area, said layer comprising polyurethane is partially non-reversibly connected to said continuous frame, wherein said partially non-reversibly connected comprises: a reversibly connecting adhesive and a non-reversibly connecting adhesive, and wherein said non-reversibly connecting adhesive is located in a distinct face or side within a perimetrical area of the continuous frame, and wherein the ratio between areas of said reversibly connecting adhesive and said non-reversibly connecting adhesive is 2:1 to 10:1; and (c) a layer opaque to UV rays having a third surface area, said third surface area covers said second surface area and is larger than said second surface area, said layer opaque to UV rays is at least partially reversibly connected to: said continuous frame, a top surface of said layer comprising polyurethane, or both, wherein said layer opaque to UV rays, said layer comprising polyurethane, or both comprises a pull-tab.

* * * * *